United States Patent [19]

Kulprathipanja

[11] Patent Number: 4,992,618
[45] Date of Patent: Feb. 12, 1991

[54] ADSORPTIVE SEPARATION PROCESS FOR THE PURIFICATION OF HEAVY NORMAL PARAFFINS WITH NON-NORMAL HYDROCARBON PRE-PULSE STREAM

[75] Inventor: Santi Kulprathipanja, Inverness, Ill.

[73] Assignee: UOP, Des Plaines, Ill.

[21] Appl. No.: 391,747

[22] Filed: Aug. 9, 1989

Related U.S. Application Data

[63] Continuation-in-part of Ser. No. 172,168, Mar. 23, 1988, abandoned.

[51] Int. Cl.$^5$ ................................................. C07C 7/13
[52] U.S. Cl. .................................... 585/820; 585/826; 585/836
[58] Field of Search ............... 585/820, 826, 835, 836; 208/310 Z, 310 R

[56] References Cited

U.S. PATENT DOCUMENTS

| | | | |
|---|---|---|---|
| 3,053,913 | 9/1962 | Norris | 260/676 |
| 3,392,113 | 7/1968 | De Rosset | 208/310 |
| 3,455,815 | 7/1969 | Fickel | 208/310 |
| 3,715,409 | 2/1973 | Broughton | 585/822 |
| 3,753,896 | 8/1973 | Bryan et al. | 585/826 X |
| 4,006,197 | 2/1977 | Bieser | 585/826 X |
| 4,021,499 | 5/1977 | Bieser | 585/828 |
| 4,436,533 | 3/1984 | Benson | 55/26 |

*Primary Examiner*—Glenn Caldarola
*Attorney, Agent, or Firm*—Thomas K. McBride; John F. Spears, Jr.; Jack H. Hall

[57] ABSTRACT

The separation of normal paraffins from non-normal hydrocarbons wherein the paraffins have from about 10 to about 35 carbon atoms per molecule, using a molecular sieve adsorbent having an effective channel diameter of about 5 angstroms wherein an improvement in the process comprises passing a non-normal hydrocarbon input stream into the adsorption zone at adsorption conditions to promote the selective adsorption of the straight chain hydrocarbon constituents of the feed material in contact with the adsorbent in preference to the lighter straight chain hydrocarbon constituents of the desorbent material also in contact with adsorbent.

21 Claims, 1 Drawing Sheet

ADSORPTIVE SEPARATION PROCESS FOR THE PURIFICATION OF HEAVY NORMAL PARAFFINS WITH NON-NORMAL HYDROCARBON PRE-PULSE STREAM

CROSS-REFERENCE TO RELATED APPLICATION

This application is a continuation-in-part of U.S. Ser. No. 172,168 filed Mar. 23, 1988.

FIELD OF THE INVENTION

The invention relates to an improved process for the separation of hydrocarbons based upon the molecular structure of the hydrocarbons. The invention relates in particular to the separation of hydrocarbons through the use of adsorptive separation in which a feed stream containing an admixture of hydrocarbons is contacted with a solid adsorbent which selectively retains one or more of the hydrocarbons. The invention specifically relates to an improved method of separating straight chain hydrocarbons from a feed mixture comprising straight chain and branched chain and aromatic hydrocarbons.

Although the applicability of the subject invention is broad, the most apparent and preferred utilization of the invention is the improvement in the degree of recovery of "heavy" norma paraffins, i.e., $C_{10}$ and higher, in the separation of normal paraffins from non-normal hydrocarbons wherein said normal paraffins have a tendency to be otherwise less completely recoverable from the feed mixture, using a molecular sieve adsorbent having a channel diameter of about 5 angstroms and a "prepulse" technique.

BACKGROUND INFORMATION

The separation of various hydrocarbonaceous compounds through the use of selective adsorbents is widely employed in the petroleum, chemical and petrochemical industries. Adsorption is often utilized when it is more difficult or expensive to separate the same compounds by other means such as by fractional distillation. Examples of such adsorptive separation processes include the separation of ethylbenzene from a mixture of xylenes, the separation of a particular xylene isomer such as paraxylene from a mixture of $C_8$ aromatics, the separation of one sugar such as glucose from a mixture of two or more sugars such as glucose and fructose, the separation of acyclic olefins from acyclic paraffins and the separation of normal paraffins from non-normal hydrocarbons including isoparaffins and cyclic paraffins. The selectively adsorbed material will normally have the same number of carbon atoms per molecule as the nonselectively adsorbed materials and will have very similar boiling points, a feature which makes separation by fractional distillation very difficult. Another common application of adsorptive separation is the recovery of a particular class of hydrocarbons from a broad boiling point range mixture of two or more classes of hydrocarbons. An example of this is the separation of $C_{10}$–$C_{14}$ normal paraffins from a mixture which also comprises $C_{10}$–$C_{14}$ isoparaffins. My invention finds specific utility recovering straight chain (normal) paraffins from a mixture comprising normal and non-normal hydrocarbon material to yield an extract material useful for further processing as candle wax, food packaging material and detergents and, in addition, a raffinate material, now depleted of such straight chain hydrocarbon material which finds utility as light lubricating oil or diesel fuel.

The adsorptive separation of various chemical compounds is a well-developed and commercially practiced process. Representative examples of such processes are provided in U.S. Pat. Nos. 3,455,815 issued to R. G. Fickel and 4,006,197 issued to H. J. Bieser. Both of these references describe processes using molecular sieve type adsorptive compounds to separate straight chain paraffins from a mixture of isoparaffins and normal paraffins. The basic separation, operating procedures, conditions, adsorbents and feed materials described in these references are similar to those which may be employed in the subject invention. Bieser '197, in particular discloses the use of a raffinate-type sweeping agent in purification zone II to flush raffinate components from the non-selective void volume of the adsorbent, to thereby achieve increased purity of the normal paraffins in the extract. U.S. Pat. No. 4,436,533 issued to R. P. Bannon is also believed pertinent for its teaching of a process, under vapor phase conditions, for the continuous adsorptive separation of normal paraffins from non-normal paraffins in a $C_{11}$ to $C_{14}$ kerosene stream. U.S. Pat. No. 3,392,113 issued to A. J. De Rosset is also believed pertinent for its teaching in regard to the adsorptive separation of normal paraffins from a hydrocarbon mixture.

U.S. Pat. No. 3,715,409 issued to Broughton, discloses a process for separating aromatic hydrocarbons using an internal raffinate stream into the adsorption zone I to displace or flush desorbent material from the adsorption zone and an internal extract stream to displace raffinate material. This raffinate input stream is preferably located near the downstream boundary of the zone, i.e., near the raffinate output stream.

U.S. Pat. No. 3,053,913 issued to Norris, is believed pertinent in connection with the purification of so-called "heavy" normal hydrocarbons, that is, according to the patentee, those straight chain hydrocarbons having at least 13 carbon atoms per molecule. Therein, Norris teaches the use of a post-adsorption, pre-desorption, adsorbent bed elution step, using, as the eluent, a liquid branched chain paraffin, preferably having between four and eight carbon atoms per molecule. Norris teaches that the eluent step washes from the non-selective volume of the adsorbent (that is, the non-selective pore volume within the adsorbent particles and the interstitial volume between adsorbent particles), the residual (unadsorbed), heavy branched chain hydrocarbon material of the feed material remaining in contact with the adsorbent as a result of the adsorption step. Such residual material, if not so washed from the sieve, would become admixed with the ultimate desired product stream during the desorption step. By employing the elution step, and therefore substituting lighter, branched chain hydrocarbon material, the ultimate product of the desorption step was easily purifiable via fractional distillation or other conventional means. Thus, Norris, like Broughton and Bieser '197, disclosed a method of increasing the purity of the heavy straight chain hydrocarbon product of a conventional adsorptive separation process. In contrast, the subject invention concerns an improved process comprising a method of increasing the recovery of straight chain hydrocarbon material of a given purity.

Also believed pertinent is U.S. Pat. No. 4,021,499, issued to Bieser, which teaches, in a process for the separation of high purity ethylbenzene from a feed mixture comprising ethylbenzene and xylene isomers, a method to increase the purity of the desired raffinate product, i.e., ethylbenzene. The method comprises the recycling of a portion of desorbent-depleted raffinate material to a point within the adsorption zone of the process, thus establishing an ethylbenzene product reflux to the system. In contrast, my invention teaches a technique of introducing a wholly external, unadsorbed, non-normal hydrocarbon stream into a process, to increase the extract product recovery of normal hydrocarbons, at a point located within the adsorption zone immediately prior to the point at which feed is introduced or even, in some instances, mixed with the feed.

BRIEF SUMMARY OF THE INVENTION

The subject invention is an improved process for separating normal and non-normal hydrocarbons through the use of adsorptive separation wherein a hydrocarbon feed material is separated into an extract material and a raffinate material through the use of a column of adsorbent having selective adsorption properties for said extract as compared to said raffinate, said improved process comprising the employment of a pre-pulse technique, such technique involving the introduction of a non-normal hydrocarbon stream which can be readily separated from the non-normal hydrocarbon feed components by simple fractionation into the column of adsorbent, prior to the point of time in the column at which the adsorbent is first contacted with the feed material, thereby resulting in a greater adsorption of the extract components of the feed material, which will, in turn, result in a higher extract material recovery. It is also contemplated that the non-normal hydrocarbon stream can be added with the feed, i.e., premixed and injected together at the feed point.

The invention is particularly useful and advantageous in separating normal paraffins from non-normal hydrocarbon feeds in which there is a range of relatively heavy components, i.e., having carbon numbers above about 10 and especially above about 20 and reducing the tendency for the lighter normal paraffins in the feed to be preferentially adsorbed over the heavier components, by reducing the competitior of the low molecular weight normal paraffins of the desorbent for the available adsorptive sites of the adsorbent.

In contradistinction to the prior art, my improved process utilizes a wholly external, non-normal hydrocarbon material and therefore unadsorbed material as the pre-pulse material, such material not necessarily being material of the type normally found in the feed mixture, but rather having the essential characteristic that when employed in the method of my invention exhibits the beneficial characteristic of enabling the extract component(s) of the feed mixture to be adsorbed, and eventually recovered, to a greater extent than would otherwise be possible without the use of my invention.

A specific embodiment of my invention comprises a process for the separation of a hydrocarbon feed material into an extract material and a raffinate material through the use of an adsorbent having selective adsorption properties for said extract material as compared to said raffinate material, said process comprising the steps of: maintaining fluid flow through a column of the adsorbent, which column comprises zones having separate operational functions occurring therein and being serially interconnected, with the terminal zones of said column connected to provide a continuous connection of said zones; maintaining an adsorption zone in said column, said zone defined by the portion of the adsorbent located between a feed input stream at an upstream boundary of said zone and a raffinate output stream at a downstream boundary of said zone; maintaining a purification zone immediately upstream from said adsorption zone, said purification zone defined by the portion of the adsorbent located between an extract output stream at an upstream boundary of said purification zone and said feed input stream at a downstream boundary of said purification zone; maintaining a desorption zone immediately upstream from said purification zone, said desorption zone defined by the portion of the adsorbent located between a desorbent input stream at an upstream boundary of said zone and said extract output stream at a downstream boundary of said zone; optionally, maintaining a buffer zone immediately upstream from said desorption zone, said buffer zone defined as the portion of the adsorbent located between the desorbent input stream at a downstream boundary of said buffer zone and a raffinate output stream at an upstream boundary of said buffer zone; passing a feed input stream comprising extract and raffinate material into the upstream end of said adsorption zone, at adsorption conditions, whereby said extract material is selectively adsorbed by the portion of the adsorbent in said zone; withdrawing a raffinate stream from the downstream end of said adsorption zone; passing a desorbent stream into the upstream end of said desorption zone, at desorption conditions, to effect the displacement of extract material from the portion of the adsorbent in said desorption zone, withdrawing an extract stream comprising extract material and desorbent material from said desorption zone, said adsorbent having adsorbed said extract material during a previous contacting of said portion of said adsorbent with the feed stream in the adsorption zone; optionally, passing at least a portion of the raffinate output stream passing out of the adsorption zone into said buffer zone; and periodically advancing through said column of adsorbent particles in a downstream direction, with respect to fluid flow in said adsorption zone, said adsorption, purification, desorption zones and, where employed, said optional buffer zone to effect a continuous separation of the feed input stream into extract and raffinate streams; wherein the improvement in said process comprises: maintaining a non-normal hydrocarbon zone within the adsorption zone of said column immediately downstream of said feed input stream, said zone defined by the portion of the adsorbent located between said feed input stream at an upstream boundary of said zone and a non-normal hydrocarbon input stream at a downstream boundary of said zone; passing a non-normal hydrocarbon input stream into said non-normal hydrocarbon zone, at the downstream boundary thereof, immediately prior to the point at which the adsorbent is contacted with said feed material at adsorption conditions to promote the selective adsorption of said extract material in contact with the adsorbent in preference to said desorbent material also in contact with adsorbent. In another embodiment said non-normal hydrocarbon can be admixed with the feed material and introduced therewith at the upstream end of said adsorption zone.

BRIEF SUMMARY OF THE FIGURES

FIG. No. 1 is a simplified process flow diagram of a simulated moving bed separation process configured in accordance with the technique of the prior art.

FIG. No. 2 is a simplified process flow diagram of a simulated moving bed separation process employing therein the preferred embodiment of my invention and showing the general relative location of a non-normal (pre-pulse) hydrocarbon zone and alternative points for the addition of a non-normal hydrocarbon stream.

DETAILED DESCRIPTION OF THE FIGURES

In FIG. No. 1, line 1 is the desorbent input to the process; line 2 is the feed to the process; line 3 is the extract product; line 4 is the raffinate product; line 6 is an optional recycle stream described below. The portions of the adsorbent vessel labelled I, II, III and IV are, respectively, the adsorption, purification, desorption zones and optional buffer zone of a simulated moving bed adsorptive separation process of the prior art. The column may contain any number of adsorbent beds, with from 8 to 24 beds of equal size being common. The number of beds in each zone may vary, depending on the separation conditions and the total number of beds being used, but with 24 beds, the adsorption zone may typically contain from 4–7 beds, the purification zone from 6–8 beds, the desorption zone from 7–9 beds and the buffer zone from 0–2 beds.

Figure 1:
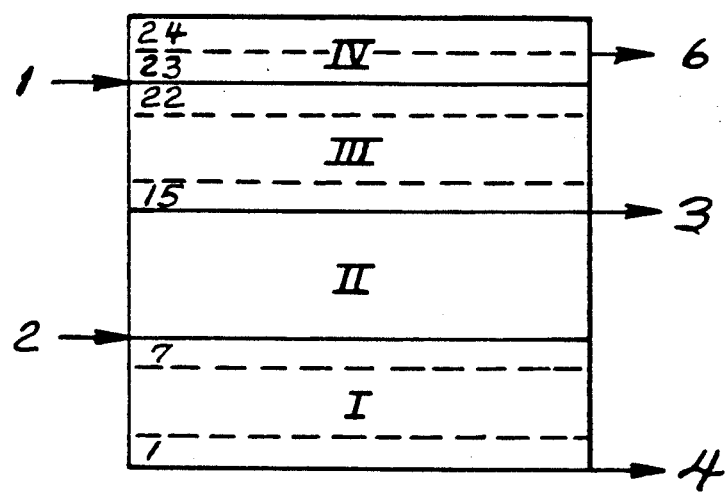

In FIG. No. 2, line 1 is the desorbent input to the process; line 2 is the feed to the process; line 3 is the extract product outlet; line 4 is the raffinate product outlet; line 5 is the non-normal hydrocarbon input (sometimes herein pre-pulse). The portions of the adsorbent vessel labelled I, II, III, and IV are, as in FIG. 1, respectively, the adsorption, purification and desorption zones and optional buffer zone of a simulated moving bed adsorptive separation process employing my invention. The portion of the adsorbent vessel labelled IA is that part of the adsorption zone lying between the feed inlet and the inlet for the non-normal hydrocarbon pre-pulse stream. In certain cases falling within the scope of this invention, this zone may become infinitesimally small or even disappear altogether, as when the pre-pulse non-normal hydrocarbon stream enters the column at the feed point just prior to introducing feed thereat or is premixed with the feed and introduced together into the adsorbent column via the feed line 2.

Line 6 is an optional recycle stream, composed mainly of desorbent which may be recycled to the process via the desorbent input stream line 1. The purpose is to create negative, or upward flow in the buffer zone to prevent raffinate materials from entering the extract product stream.

Line 7 is a flush stream input which corresponds to the teachings of the aforementioned Bieser Pat. No. 4,006,197, illustrated in comparative Example IV of this application. Line 8 is a raffinate-type material input stream close to the raffinate output stream 4, illustrated in Comparative Example V of this application.

Although any number of beds in the column may be selected, to achieve an economical and efficient separation with this invention, from 8 to 24 beds are preferred. The number of beds in each zone might be selected as in the illustration of a 24-bed column above, in which the non-normal hydrocarbon zone IA may consist of from zero to two of the beds of the adsorption zone nearest the feed inlet 2. Recycle stream line 6 is positioned in the middle of the optional zone, if used. Flush stream input line 7 can be positioned 1 or 2 beds downstream of the extract outlet 3. Raffinate-type material input stream line 8 can be positioned 1 or 2 beds upstream of the raffinate product outlet line 4.

DETAILED DESCRIPTION OF THE INVENTION

In my improved adsorptive separation process, normal paraffins, i.e., straight chain hydrocarbons, of the feed material, are selectively adsorbed onto the adsorbent in preference to the non-normal hydrocarbon material also present in the liquid with which the adsorbent is in contact. If hydrocarbon material of only a single carbon number were in contact with such adsorbent, the adsorption would proceed eventually to the equilibrium separation dictated by the adsorptive system used. Furthermore, in such case, the particular process conditions would be chosen so as to achieve the desired approach to equilibrium in view of the relative adsorption characteristics of the feed material in question. Hence, the normal hydrocarbons present in the feed material would be recovered to the degree desired and not lost to the raffinate stream. However, in practice, a compromise must be made as the feed material comprises a mixture not only with respect to molecular orientation, but also with respect to molecular weight. Accordingly, because of the mass transfer characteristics of the adsorbent with respect to each of the various feed mixture components, a given adsorbent will tend to adsorb straight chain hydrocarbons of a relatively low molecular weight, in preference to those of relatively higher molecular weight (and of course, with respect to any given molecular weight, normal hydrocarbons are preferentially adsorbed over non-normal hydrocarbons). This appears to be due to the relative ease with which the smaller, more mobile molecules of the relatively low molecular weight, straight chain hydrocarbon material traverse the selective pore openings. In practice then, the recovery of normal paraffins of a given carbon number is dependent upon the carbon number of the normal paraffin in question. This phenomena poses commercial problems insofar as, in broad carbon number range feed mixtures, and, more especially, in relatively heavy feed mixtures, the higher carbon number feed components are not recovered to the desired degree, i.e., to the same extent as the lower carbon number feed components, when adsorption separation processes of the prior art are employed.

A specific case illustrating this problem occurs in the separation of straight chain hydrocarbon material from a mixture comprising straight and branched chain hydrocarbon material, wherein such mixture comprises hydrocarbons having between about 10 and about 35 carbon atoms per molecule. In such case, the recovery of straight chain material, (that is the amount, on a weight basis, of straight chain hydrocarbon material of a given molecular weight recovered in the extract product stream relative to the amount of such straight chain hydrocarbon material present in the feed to the process), is found to be roughly inversely related to the number of carbon atoms per molecule of the straight chain material in question. Although such phenomenon likely occurs in all multiple carbon number feed mixtures, it is most apparent in the case hereinabove illustrated due to the exaggerated effect of high molecular weight on straight chain hydrocarbon recovery. In other words, the effect of relatively high molecular weight upon straight chain hydrocarbon recovery, although manifested at all carbon numbers, is only practically measurable and thus usually commercially significant at carbon numbers of about 10 or more and most significant at carbon numbers of about 14 or more. Although recovery of straight chain hydrocarbon material may be enhanced by operation at higher temperatures, the recovery of the heavier straight chain hydrocarbon material at some point becomes commercially unviable or may, with very heavy material, ultimately approach zero, due to the very low mass transfer of such heavy straight chain material into and/or out of the selective pores of the adsorbent.

It is therefore an object of my invention to provide an improved process for the adsorptive separation of normal paraffins from a feed mixture comprising normal and non-normal hydrocarbons such that the overall recovery of the normal paraffins is enhanced. It is a further object of my invention to provide an improvement in the recovery of relatively high molecular weight straight chain hydrocarbon material contained in the feed mixture. These objectives are met by the employment of a technique which is herein otherwise referred to as a "pre-pulse" technique.

The feed stream to my process must comprise a mixture of normal paraffins and non-normal hydrocarbons. The non-normal hydrocarbons may include cyclic compounds and/or branched chained hydrocarbons. The feed stream has preferably been purified, as by hydrotreating, to remove any significant quantity of sulfur, oxygen, nitrogen or olefinic compounds. The feed stream will normally have a carbon number range of three or more. Typical feeds are a mixture of $C_{10}$ through $C_{14}$ paraffins, $C_{13}$ through $C_{30}$ paraffins, a mixture of $C_{15}$ through $C_{25}$ paraffins, a mixture of $C_{24}$ through $C_{26}$ paraffins or $C_{26}$ through $C_{28}$ paraffins and non-normal hydrocarbons in the same boiling point range. Since the branched chain and alicyclic hydrocarbons have slightly different boiling points from their respective normal hydrocarbons having the same carbon number, the non-normal hydrocarbons will have a similar though slightly displaced carbon number range. Aromatic hydrocarbons may be present, as well. In other words, the feed stream may contain normal paraffins having carbon numbers in the range from about 10 up to about 35 or more and non-normal hydrocarbons in about the same range.

Adsorptive separation processes may be performed using a variety of operating techniques. For instance, the adsorbent may be retained as a fixed bed or transported through the adsorption zone as a moving bed. In addition, techniques may be employed to simulate the movement of the adsorbent bed. The adsorptive separation zone can therefore comprise a simple swing-bed system with one or more beds of adsorbent being used to collect the desired chemical compound(s) while previously used beds are being regenerated by the use of a desorbent and possibly by a simultaneous temperature increase, pressure decrease, or a combination of two or more of these commonly used regeneration techniques. A further possible variation in the operation of the adsorptive separation zone results from the possibility of operating the adsorbent beds under either vapor phase or liquid phase conditions. The use of liquid phase methods is preferred. Certain benefits are obtained by using a simulated moving bed of adsorbent. These benefits include the continuous production of a high purity product stream while avoiding attrition of the adsorbent. Preferably, the countercurrent flow of the bed of solid adsorbent and the various entering liquid streams, such as the feed and desorbent streams, is simulated.

Two separate actions are involved in this simulation. The first of these is the maintenance of a net fluid flow through the bed of adsorbent in a direction opposite to the direction of simulated movement of the adsorbent. This is performed through the use of a pump operatively connected in a manner to achieve this circulation along the length of the entire bed of adsorbent. The second action involved in simulating the movement of the adsorbent is the periodic actual movement of the location of the various zones, such as the adsorption zone, along the length of the bed of adsorbent. This actual movement of the location of the various zones is performed step-wise in a unidirectional pattern by periodically advancing the points at which the entering streams enter the adsorbent bed and the points at which the effluent streams are withdrawn from the adsorbent bed. It is only the locations of the zones as defined by the respective entry and withdrawal points along the bed of adsorbent which are changed. The adsorbent bed itself is fixed and does not move.

The bed of adsorbent may be contained in one or more separate interconnected vessels, typically 8–24. At a large number of points along the length of the bed of adsorbent, the appropriate openings and conduits are provided to allow the addition or withdrawal of liquid. At each of these points, there is preferably provided a constriction of the cross-section of the bed of adsorbent by a liquid distributor-collector. These may be similar to the apparatus described in U.S. Pat. Nos. 3,208,833; 3,214,247; and 3,523,762. These distributor-collectors serve to aid in the establishment and maintenance of plug flow of the fluids along the length of the bed of adsorbent. The two points at which any one stream enters and the corresponding effluent stream leaves the bed of adsorbent are separated from each other by at least two or more potential fluid feed or withdrawal points which are not being used.

The gradual and incremental movement of the adsorption zone is achieved by periodically advancing the actual points of liquid addition or withdrawal to the next available potential point. That is, in each advance of the adsorption zone, the boundaries marking the beginning and the end of each zone will move by the relatively uniform distance between two adjacent potential points of liquid addition or withdrawal. The majority of the zone is unaffected and remains intact since the zone extends past several of these fluid transfer points.

The switching of the fluid flows at these many different locations may be achieved by a multiple-valve manifold or by the use of a multiple-port rotary valve. A central digital controller is preferably used to regulate the operation of the rotary valve or manifold.

As used herein, the term "feed stream" is intended to indicate a stream in the process which comprises the feed material and which is charged to the bed of adsorbent for the purpose of recovering the extract component. The feed stream will comprise one or more extract components and one or more raffinate components. An "extract component" is a chemical compound which is preferentially adsorbed by the adsorbent which is being used as compared to a "raffinate component". Normally the term "extract component" is synonymous with the desired product of the process. For instance, in the preferred embodiment of the subject process, normal paraffins are selectively adsorbed compared to non-normal hydrocarbons and are the extract component which is recovered as a product. The other chemical compounds which were contained in the feed stream, which in the preferred embodiment are usually, mainly isoparaffins, become the raffinate components. In the case at hand the isoparaffin-rich raffinate would often also be considered a final product due to its use as a high octane motor fuel or blending component, while the extract could be charged to a paraffin isomerization stage or as feed material to a fatty acid, chloroparaffin or alpha olefin process, or used in some other manner, e.g., as mentioned previously.

The term "extract stream" refers to a stream which contains extract components originally contained in the feed stream and which have been desorbed from the bed of adsorbent by the desorbent stream. The composition of the extract stream as it leaves the bed of adsorbent will normally vary with time and can range from about 100 mole percent extract components to about 100 mole percent desorbent components. The term "raffinate stream" is intended to indicate a stream originating at the bed of adsorbent and which contains the majority of the raffinate components of the feed stream. The raffinate stream is basically the unadsorbed components of the feed stream and non-normal hydrocarbon input stream and desorbent components which are picked up during passage through the adsorption zone. Both the extract stream and the raffinate stream are normally passed into a backmixed accumulation zone before being passed into the respective fractionation columns.

The term "non-normal hydrocarbon input stream" refers to a stream which has a normal hydrocarbon concentration lower than the concentration of normal hydrocarbons at the point at which it enters the bed of adsorbent and, preferably, is essentially free of normal hydrocarbon material. This stream is preferably introduced into the adsorbent column just prior to contact by the adsorbent by the feed stream, or with the feed stream, and can be 1 or 2 beds downstream from the feed or it can be introduced as a pulse by interrupting the feed stream and introducing the non-normal hydrocarbon stream in the feed inlet before the feed is introduced. As shown in the examples herein, it is also possible, within the scope of this invention, to premix the non-normal hydrocarbon stream with the feed and introduce both at the feed inlet simultaneously whereby the same advantage and results referred to herein can be achieved. One function accomplished by this stream is to flush low molecular weight normal hydrocarbons which originate from the desorbent from the void volume of the adsorbent and thereby locally lower the concentration of such normal hydrocarbons in the liquid surrounding the adsorbent particles. This reduction in concentration of low molecular weight desorbent n-paraffins apparently reduces the competition between relatively heavier normal hydrocarbons of the feed and such relatively lighter normal hydrocarbons for the available selective pores of the adsorbent, thus allowing for increased recovery of the heavier normal hydrocarbon material. Hence, the relatively higher molecular weight normal hydrocarbons originating in the feed source are adsorbed (and therefore eventually recovered as extract product) to a greater degree than would be the case without the use of such prepulse technique. Thus, the total recovery of the normal paraffins in the feed is substantially improved, due to the increased recovery of the heavier normal paraffins contained in the feed.

The preferred materials for the non-normal hydrocarbon stream are branched paraffins having a lower boiling point than the feed, to make the recovery thereof from the extract easier since they can be separated by conventional fractionation means. More preferably, the non-normal hydrocarbon is the same non-normal hydrocarbon used in the desorbent, since that will further simplify the recovery of this material from the extract and raffinate streams. Other non-normal hydrocarbons which can be used are cyclic aliphatic, or alicyclic, hydrocarbons and aromatic hydrocarbons having a boiling point lower than the feed, as well as mixtures thereof.

As used herein, the term "desorbent" is intended to indicate a chemical compound capable of desorbing the extract component from the bed of adsorbent. A "desorbent stream" is a process stream in which the desorbent is carried to the bed of adsorbent. The desorbent is preferably a hydrocarbon which may be separated from the extract and the raffinate components quite readily by fractional distillation. The desorbent should therefore have a different carbon number, preferably less, than the extract component. In the preferred embodiment of separating normal and non-normal paraffins, the desorbent stream is preferably rich in normal paraffins having molecular weights, i.e. carbon numbers, lower than those in the feed stream and should have a mol ratio of normal paraffins to non-normal isoparaffins and cyclic hydrocarbons, above about 2:1. The preferred normal paraffins in the desorbent are $C_{4-8}$ and, particularly, $C_5$, $C_6$ or $C_7$. The preferred non-normal hydrocarbons in the desorbent, when used, are branched chain paraffins having lower molecular weights, i.e., carbon numbers, than those in the feed stream. Especially preferred are branched chain paraffins having from 4-8 carbons in the molecule, e.g., iso-butane, iso-pentane, iso-hexane, iso-octane.

A preferred configuration for the adsorptive separation zone and the preferred simulated moving bed technique is described in some detail in the previously referred to U.S. Pat. Nos. 3,392,113; 3,455,815; and 4,006,197 and 2,985,589 which are incorporated herein by reference. These references describe suitable operating conditions and methods and suitable adsorbents for use in the separation of isoparaffins and other non-normal hydrocarbons, such as aromatics, from normal paraffins. Further information on adsorptive techniques and the preferred operating methods may be obtained by reference to U.S. Pat. Nos. 3,617,504; 4,133,842; and 4,434,051, which are incorporated herein by reference. Information on a suitable rotary valve design is available in U.S. Pat. No. 3,040,777. An entirely different type of simulated moving bed adsorptive separation which can be employed to recover either isoparaffins or normal paraffins is described in U.S. Pat. Nos. 4,402,832 and 4,498,991, which process simulates a continuous cocurrent movement of the adsorbent relative to the fluid flow, whereas the preferred adsorptive separation technique utilizes simulated countercurrent movement of the adsorptive material in fluid flows.

The preferred operating conditions for the adsorbent containing chambers used in the separation step include a temperature of from 25 to about 350 degrees Celsius and a pressure of from atmospheric to about 3000 kPa g. The pressure is normally set as being sufficient to maintain liquid phase conditions within all points of the adsorptive separation process. A temperature of from 120 to 250 degrees Celsius and a pressure between 600 and 7500 kPa g are more preferred. A temperature from 185° C. to 225° C. is most preferred. It was also observed in pulse tests simulating the invention that the net retention volume was fairly uniformly reduced by about 4 ml for all normal hydrocarbons having carbon numbers in the range from 10 to 20 when the temperature was raised from 185° C. to 225° C. This indicates a higher rate of desorption and thus, a shorter possible cycle time. The adsorbents which are preferred for the separation of normal paraffinic hydrocarbon from non-paraffinic hydrocarbons have relatively uniform pore diameters of about 5 angstroms such as the commercially available type 5A molecular sieves produced by the molecular sieve division of UOP, formerly Linde Division of Union Carbide Corporation.

For best results in the practice of the process, it has been found that the ratio, Lp/A, where Lp is the flow rate of the prepulse input stream and A is the (simulated) flow rate of the adsorbent, should be between 4 and 5. Thus, in the examples, where A was 55 ml/hr, Lp is preferably 220–275 ml/hr.

The following examples are merely illustrative embodiments of my invention and as such are not meant to limit or otherwise restrict the applicability of my invention.

EXAMPLE I (Prior Art)

Figure 2:
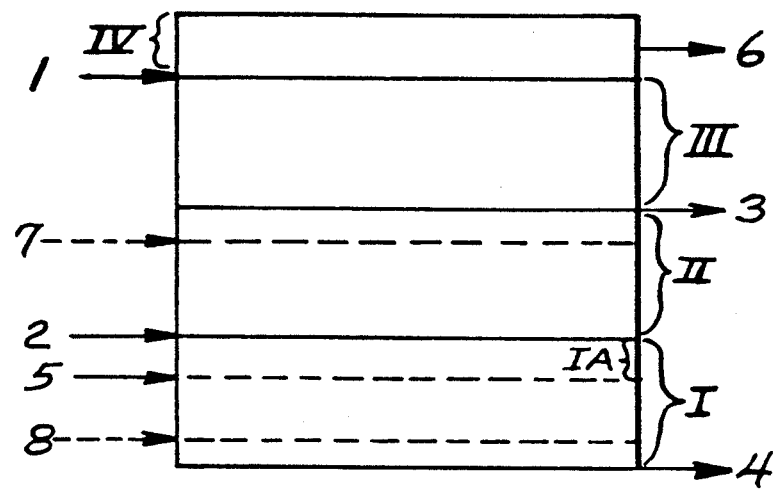

The following pilot plant data was obtained without the use of my invention and therefore provides a reference point to judge the utility of my pre-pulse technique relative to that of the prior art. A simulated moving bed adsorptive separation pilot plant, of the type schematically represented by FIG. No. 1, consisting of 24 beds located vertically with the top and bottom beds connected for continuous flow was loaded with 460 cc of UOP type 5A adsorbent and operated at a temperature of 200 degrees Celsius, pressure of about 2100 kPa g and a rotary valve cycle time of 1 hour. In this configuration, the adsorption zone consisted of 7 beds, the purification zone consisted of 7 beds, the desorption zone consisted of 8 beds and the optional buffer zone consisted of 2 beds. Counting the beds from the bottom and referring to FIG. 1 for the input and output streams, at the beginning of the cycle as feed was injected into the top of bed 7, raffinate was withdrawn from the bottom of bed 1, desorbent was injected into the top of bed 22 and extract was withdrawn from the bottom of bed 15. Flow in all zones except the buffer zone IV was downward; in the buffer zone IV flow was negative, or upward, in order to prevent raffinate from entering the extract stream. A recycle stream 6, as shown in FIG. 2, was removed from the top of bed 23 and recycled to the bottom of bed 23 as desorbent. Periodically, the recycle stream was removed from the process and additional fresh desorbent was added instead. This establishes the negative flow in zone IV and decreases the amount of desorbent that must be removed from the raffinate by fractionation, but does not otherwise affect the raffinate purity. The feed material was a synthetic blend of n-$C_{22}$, n-$C_{28}$ and a mixture of isoparaffins (i-$C_{10-17}$) having a carbon number range from $C_{10}$ to $C_{17}$. The composition (wt.%) and flow rates of the various streams are tabulated in Table 1.

TABLE 1

| Component/Stream (wt. %) | Feed | Extract | Raffinate | Desorbent |
|---|---|---|---|---|
| n-$C_{22}$ | 35 | 2.1 | 1.8 | 0 |
| n-$C_{28}$ | 35 | 0.6 | 3.4 | 0 |
| i-$C_{10-17}$ | 30 | 0.1 | 3.8 | 0 |
| iso-octane | 0 | } 97.2 | } 91.0 | 30 |
| n-octane | 0 | | | 70 |
| Total | 100 | 100 | 100 | 100 |
| Flow Rates (cc/hr) | 35 | 363 | 300 | 586 |
| Pre-pulse | | NONE | | |

From the data above, the purity of the normal paraffins in the extract was calculated to be 96.4%. Recovery of normal paraffins was 39%.

EXAMPLE II

The same simulated moving bed pilot plant used in Example I, above, was configured for the practice of my pre-pulse technique. This was accomplished by the introduction of a non-normal hydrocarbon inlet stream (having the composition and at the flow rate shown below) through line 5 of FIG. 2 into the top of bed 6 of the absorbent column, i.e., one bed below the feed inlet. The other streams remained as in Example I and the same adsorbent type and amount, cycle time, feed and desorbent compositions, temperature and pressure as used in Example I were used in this Example II. The compositions (wt.%) and flow rates of the various streams are tabulated in Table 2.

TABLE 2

| Component/Stream (wt. %) | Feed | Extract | Raffinate | Desorbent |
|---|---|---|---|---|
| n-$C_{22}$ | 35 | 3.0 | 0.7 | 0 |
| n-$C_{28}$ | 35 | 1.9 | 1.4 | 0 |
| iso-$C_{10-17}$ | 30 | 0.1 | 2.2 | 0 |
| iso-octane | 0 | } 95.0 | } 95.7 | 30 |
| n-octane | 0 | | | 70 |
| Total | 100 | 100 | 100 | 100 |
| Flow Rates (cc/hr) | 35 | 367 | 548 | 583 |
| Pre-pulse Flow Rate (100% Iso-Octane) | | | | 247 cc/hr |

In this example, purity of normal paraffins in the extract was 98%. Recovery was 61%.

DISCUSSION OF EXAMPLES I AND II

As can be seen from the above data, the employment of my invention significantly improves the ability of a given adsorbent/desorbent combination to selectively adsorb normal paraffins from a mixture of normal and non-normal hydrocarbons. Specifically, comparing the data of Example II to that of Example I, the recovery of n-$C_{22}$ and n-$C_{28}$ hydrocarbons initially present in the feed stream is significantly higher in Example II than that demonstrated in Example I, using the same apparatus and under the same other operating conditions, but without the use of my invention.

It is also important to note that, without the use of my invention, not only is the total normal paraffin recovery diminished but also, the recovery of individual normal paraffins initially present in the feed are clearly shown to vary in an inverse relationship to the carbon number of the normal paraffin in question. Contrastingly, Example II indicates that, within the carbon number range tested, the use of my invention substantially reduces this disparity. Further, as will be shown in later Example VI, this disparity can be eliminated and both normal heavier and lighter paraffins can be recovered to the same extent.

EXAMPLE III

Example II was repeated except that the non-normal hydrocarbon feed was mixed with the feed and introduced into the top of bed 7 of the adsorbent column with the feed stream 2. The composition and flow rates of the various streams are tabulated in Table 3 below and demonstrate that the improved results of the invention are achieved by this embodiment.

TABLE 3

| Component/Stream (wt. %) | Feed | Extract | Raffinate | Desorbent |
|---|---|---|---|---|
| n-$C_{22}$ | 35 | 3.3 | 0.7 | 0 |
| n-$C_{28}$ | 35 | 1.9 | 1.9 | 0 |
| iso-$C_{10-17}$ | 30 | 0.2 | 2.8 | 0 |
| iso-octane | 0 | 94.6 | 94.6 | 30 |
| n-$C_8$ | 0 | | | 100 |
| Flow Rates (cc/hr) | 35 | 393 | 365 | 581 |
| Non-normal HC Flow Rate (100% iso-octane) | | | | 240 cc/hr |

Purity of the extract product was 96.3% and recovery was 68.2%.

EXAMPLE IV (Comparative)

The same simulated moving bed pilot plant used in Example II, above, was modified so as to introduce a non-normal hydrocarbon stream into the purification zone II of the adsorbent column through line 7 (FIG. 2), two beds below (downstream of) the extract output line 3, in the manner in which Bieser Pat. No. 4,006,197 teaches the introduction of a "raffinate-type sweeping agent". The same non-normal hydrocarbon stream (100% iso-octane), adsorbent type and amount, cycle time and feed and desorbent compositions used in Example II were used in this Example. Compositions (wt.%) and flow rates in Table 4 are the averages of three runs.

TABLE 4

| Component/Stream (wt. %) | Feed | Extract | Raffinate | Desorbent |
|---|---|---|---|---|
| n-$C_{22}$ | 35 | 1.97 | 1.2 | 0 |
| n-$C_{28}$ | 35 | 0.97 | 2.23 | 0 |
| iso-$C_{10-17}$ | 30 | Trace | 2.63 | 0 |
| iso-octane | 0 | 97.0 | 93.94 | 30 |
| n-$C_8$ | 0 | | | 70 |
| Flow Rates (cc/hr) | 35 | 466 | 448 | 576 |
| Sweeping Agent Flow Rate (100% iso-octane) | | | | 240 cc/hr |

From the data above, purity and recovery were calculated to be 99% and 47.1%, respectively. Although a high purity extract may be obtained, as disclosed by Bieser, the recovery is quite low.

EXAMPLE V (Comparative)

The safe simulated moving bed pilot plant used in Example II, above, was modified so as to introduce a non-normal hydrocarbon stream into the adsorption zone I of the adsorbent column through line 8 (FIG. 3), one bed above (upstream of) the raffinate stream 4 and five beds below (downstream of) the feed stream 2, to demonstrate the effects of introducing the non-normal hydrocarbon stream at a point in the adsorption zone remote from the feed point. The same non-normal hydrocarbon stream (100% iso-octane), adsorbent type and amount, cycle time and feed and desorbent compositions used in Example II were used in this example. The compositions (wt.%) and flow rates tabulated below in Table 5 are the averages of three runs.

TABLE 5

| Component/Stream (wt. %) | Feed | Extract | Raffinate | Desorbent |
|---|---|---|---|---|
| n-$C_{22}$ | 35 | 2.33 | 0.73 | |
| n-$C_{28}$ | 35 | 0.47 | 1.40 | |
| iso-$C_{10-17}$ | 30 | 0.1 | 1.43 | |
| iso-octane | 0 | 97.1 | 96.44 | 30 |
| n-$C_8$ | 0 | | | 70 |
| Flow Rates (cc/hr) | — | 568.7 | 363.3 | 585 |
| Non-normal HC Flow Rate (100% iso-octane) | | | | 240 cc/hr |

Purity of the extract product was 99% and recovery was 46.7%. Again, high purity can be achieved, but recovery is lower than can be achieved with the instant process.

EXAMPLE VI

Example III, using the same pilot plant configured for practicing the invention, was repeated, except that 100% n-hexane was used as the desorbent. This resulted in separating the normal (n-$C_{22}$ and n-$C_{28}$) paraffins from the feed with 97.4% purity and higher recovery of 95.7%. Also, as can be seen from Table 6, below, the heavier normal paraffin component, n-$C_{28}$, is recovered in the same amount as the lighter normal paraffin and total recovery of normal paraffins is greater than obtained using prior methods such as illustrated in Example I. The composition (wt.%) and flow rates of the various streams are set forth in Table 6.

TABLE 6

| Component/Stream (wt. %) | Feed | Extract | Raffinate | Desorbent |
|---|---|---|---|---|
| n-$C_{22}$ | 35 | 3.8 | 0.2 | 0 |
| n-$C_{28}$ | 35 | 3.8 | 0.1 | 0 |
| iso-$C_{10-17}$ | 30 | .2 | 2.9 | 0 |
| iso-octane | 0 | 0 | 75 | 0 |
| n-hexane | 0 | 92.2 | 21.8 | 100 |
| Total | 100 | 100 | 100 | 100 |
| Flow Rates (cc/hr) | 35 | 366 | 414 | 588 |
| Pre-pulse Flow Rate (100% Iso-Octane) | | | | 240 cc/hr |

In this example, purity of normal paraffins in the extract was 97.4%. Recovery was 95.7%.

EXAMPLE VII

Example VI was repeated, using instead, as the feed, a gas oil fraction which analyzed 69.2 wt.% normal $C_{20}$-$C_{30}$ and 31.8 wt.% of non-normal hydrocarbons (HC) boiling in the same range. On a desorbent-free basis, the extract was 99.8% normal $C_{20-30}$ paraffins and recovery was 86%. The feed and extract compositions are set forth in Table 7.

TABLE 7

| Component/Stream (wt. %) | Feed | Extract | Raffinate | Desorbent |
|---|---|---|---|---|
| n-$C_{20}$ | 0.1 | 0.01 | — | 0 |
| n-$C_{21}$ | 0.8 | 0.17 | — | 0 |
| n-$C_{22}$ | 4.3 | 0.95 | — | 0 |
| n-$C_{23}$ | 10.0 | 2.19 | — | 0 |
| n-$C_{24}$ | 13.6 | 2.99 | — | 0 |
| n-$C_{25}$ | 16.8 | 3.35 | — | 0 |
| n-$C_{26}$ | 12.4 | 2.79 | — | 0 |
| n-$C_{27}$ | 7.7 | 1.73 | — | 0 |
| n-$C_{28}$ | 2.7 | 0.6 | — | 0 |

TABLE 7-continued

| Component/Stream (wt. %) | Feed | Extract | Raffinate | Desorbent |
|---|---|---|---|---|
| n-C$_{29}$ | 0.7 | 0.16 | — | 0 |
| n-C$_{30}$ | 0.1 | 0.03 | — | 0 |
| non-normal HC | 31.8 | 0.03 | — | 0 |
| iso-octane | 0 | 85.03 | — | 0 |
| n-hexane | 0 | | — | 100 |
| Flow Rates (cc/hr) | 33 | 163 | 400 | 389 |
| Pre-pulse Flow Rate (100% iso-octane) | | | | 253 cc/hr |

Excellent recovery was achieved with very high purity using this process, which included premixing the non-normal pulse stream with the feed and using the preferred desorbent, n-hexane.

I claim as my invention:

1. In a process for separating normal paraffin hydrocarbons from non-normal hydrocarbons with increased recovery of said normal hydrocarbons through the use of adsorptive separation wherein a hydrocarbon feed material comprising normal paraffins and non-normal hydrocarbons having a range of carbon numbers greater than 10, is separated into an extract material comprising relatively adsorbed normal hydrocarbons and a raffinate material comprising the relatively non-adsorbed non-normal hydrocarbons using a column of adsorbent having selective adsorption properties for the extract material as compared to the raffinate material comprising contacting said adsorbent with said feed material, removing said relatively non-adsorbed non-normal hydrocarbons from said adsorbent and desorbing said adsorbed normal paraffin hydrocarbons with a desorbent comprising a normal hydrocarbon having lower carbon numbers than said feed material, the improvement comprising passing a non-normal hydrocarbon input stream having lower carbon numbers than said feed material into the adsorption zone of said column of adsorbent at the upstream end of said adsorption zone prior to the point at which said adsorbent is contacted with the feed material or mixed with feed material whereby the normal hydrocarbons comprising said desorbent are substantially diluted in the void volume and said normal paraffin constituents of said feed material in contact with the adsorbent are adsorbed in preference to said desorbent normal hydrocarbons also in contact with adsorbent to thereby increase the recovery of said normal paraffin hydrocarbon feed materials.

2. In a process for separating normal paraffin hydrocarbons from non-normal hydrocarbons through the use of adsorptive separation wherein a hydrocarbon feed material is separated into an extract material and a raffinate material using a column of adsorbent having selective adsorption properties for the extract material as compared to the raffinate material, comprising introducing a non-normal hydrocarbon input stream into the column of adsorbent, immediately prior to the point at which the adsorbent is contacted with said feed material to promote the selective adsorption of said normal paraffin hydrocarbon constituents of said feed material in contact with the adsorbent in preference to the normal hydrocarbon constituents of a desorbent material also in contact with adsorbent.

3. The process of claim 1 further characterized in that said adsorbent comprises type 5A molecular sieves.

4. The process of claim 1 further characterized in that said feed material comprises straight chain molecules having between 10 and 35 carbon atoms per molecule 5. The process of claim 1 further characterized in that said hydrocarbon feed material comprises straight chain molecules having between 20 and 30 carbon atoms per molecule.

6. The process of claim 1 further characterized in that said non-normal hydrocarbon input stream comprises branched chain hydrocarbon material which is readily separable from the feed material by fractionation means.

7. The process of claim 6 further characterized in that said non-normal hydrocarbon input stream is fed to the adsorption zone at a rate such that the ratio of the flow rate to the adsorbent flow rate, Lp/A, is from 4 to 5.

8. The process of claim 1 further characterized in that said non-normal hydrocarbon input stream is essentially free of straight chain hydrocarbon material.

9. The process of claim 1 further characterized in that it is practiced in a batch manner.

10. The process of claim 1 further characterized in that it is practiced in a moving bed manner.

11. The process of claim 10 further characterized in that it is practiced in a simulated moving bed manner.

12. The process of claim 10 further characterized in that it is practiced in a countercurrent or cocurrent manner.

13. A process for the separation of a hydrocarbon feed material into an extract material and a raffinate material through the use of an adsorbent having selective adsorption properties for said extract material as compared to said raffinate material, said process comprising:

(i) maintaining fluid flow through a column of the adsorbent, which column comprises zones having separate operational functions occurring therein and being serially interconnected, with the terminal zones of said column connected to provide a continuous connection of said zones;

(ii) maintaining an adsorption zone in said column, said zone defined by the portion of said adsorbent located between a feed input stream at an upstream boundary of said zone and a raffinate output stream at a downstream boundary of said zone;

(iii) maintaining a purification zone upstream from said adsorption zone, said purification zone defined by the portion of the adsorbent located between an extract output stream at an upstream boundary of said purification zone and said feed input stream at a downstream boundary of said purification zone;

(iv) maintaining a desorption zone immediately upstream from said purification zone, said desorption zone defined by the portion of the adsorbent located between a desorbent input stream at an upstream boundary of said zone and said extract output stream at a downstream boundary of said zone;

(v) optionally, maintaining a buffer zone immediately upstream from said desorption zone, said buffer zone defined as the portion of the adsorbent located between the desorbent input stream at a downstream boundary of said buffer zone and a raffinate output stream at an upstream boundary of said buffer zone;

(vi) passing a feed input stream comprising extract and raffinate material into the upstream end of said adsorption zone, at adsorption conditions, whereby said extract material is selectively adsorbed by the portion of the adsorbent in said zone;

(vii) withdrawing a raffinate material from the downstream end of said adsorption zone;

(viii) passing a desorbent stream into the upstream end of said desorption zone, at desorption conditions, to effect the displacement of extract material from the portion of the adsorbent in said desorption zone;

(ix) withdrawing an extract stream comprising extract material and desorbent material from the downstream end of said desorption zone, said adsorbent having adsorbed said extract material during a previous contacting of said portion of said adsorbent with the feed stream in the adsorption zone;

(x) optionally, passing at least a portion of the raffinate output stream passing out of the adsorption zone into said buffer zone; and (xi) periodically advancing through said column of adsorbent particles in a downstream direction, with respect to fluid flow in said adsorption zone, said adsorption, purification, desorption zones and, where employed, said optional buffer zone to effect a continuous separation of said feed input stream into extract and raffinate streams; wherein the improvement in said process comprises: maintaining a non-normal hydrocarbon zone within the adsorption zone of said column immediately downstream of said feed input stream, said zone defined by the portion of the adsorbent located between said feed input stream at an upstream boundary of said zone and a non-normal hydrocarbon input stream at a downstream boundary of said zone; passing a non-normal hydrocarbon input stream into said non-normal hydrocarbon zone, at the downstream boundary thereof, at adsorption conditions, to promote the selective adsorption of said extract material in contact with the adsorbent in preference to said desorbent material also in contact with said adsorbent.

14. The process of claim 13 further characterized in that said adsorbent comprises 5A molecular sieves.

15. The process of claim 13 further characterized in that said non-normal hydrocarbon input stream is immediately prior to the point at which the adsorbent is contacted with said feed material.

16. The process of claim 15 further characterized in that said extract material comprises normal paraffin hydrocarbon molecules having between 10 and 35 carbon atoms per molecule and said raffinate material comprises non-normal hydrocarbons having boiling points with the same range as said normal paraffin hydrocarbons.

17. The process of claim 16 further characterized in that said normal paraffin hydrocarbon extract material comprises molecules having between 20 and 30 carbon atoms per molecule 18. The process of claim 13 further characterized in that said desorbent comprises normal hydrocarbons having a lower boiling point than said feed material.

19. The process of claim 13 further characterized in that said non-normal hydrocarbon input stream comprises branched chain hydrocarbons which are readily separable from the feed material by fractionation means.

20. The process of claim 13 further characterized in that said non-normal hydrocarbon input material is essentially free of straight chain hydrocarbon material.

21. The process of claim 1 wherein normal feed materials having a higher carbon number are selectively adsorbed to the same extent that normal feed materials having a lower carbon number are adsorbed.

* * * * *